(12) United States Patent
Galperin

(10) Patent No.: US 8,775,451 B2
(45) Date of Patent: Jul. 8, 2014

(54) OBJECT BASED IMAGE RETRIEVAL

(75) Inventor: Michael Galperin, Vista, CA (US)

(73) Assignee: Almen Laboratories, Inc., Vista, CA (US)

( * ) Notice: Subject to any disclaimer, the term of this patent is extended or adjusted under 35 U.S.C. 154(b) by 955 days.

(21) Appl. No.: 11/841,888

(22) Filed: Aug. 20, 2007

(65) Prior Publication Data
US 2008/0037876 A1 Feb. 14, 2008

Related U.S. Application Data

(63) Continuation of application No. 11/007,062, filed on Dec. 7, 2004, now Pat. No. 7,483,919, which is a continuation-in-part of application No. 09/370,366, filed on Aug. 9, 1999, now Pat. No. 6,941,323.

(51) Int. Cl.
*G06F 17/30* (2006.01)

(52) U.S. Cl.
USPC .................................. 707/758; 707/999.107

(58) Field of Classification Search
CPC .................. G06T 7/0012; G06T 2207/30004; Y10S 707/99933; Y10S 707/99936; Y10S 707/99931; G06F 17/3025; G06F 17/30259; G06F 17/06
USPC .......... 600/407, 481, 437; 382/132, 128, 203, 382/209, 260, 294, 217, 118; 707/758, 600; 345/635, 555, 156
See application file for complete search history.

(56) References Cited

U.S. PATENT DOCUMENTS

| | | | |
|---|---|---|---|
| 4,907,156 A | 3/1990 | Doi et al. | |
| 5,019,975 A | 5/1991 | Mukai | |
| 5,133,020 A | 7/1992 | Giger et al. | |
| 5,179,651 A * | 1/1993 | Taaffe et al. | 345/555 |
| 5,289,374 A | 2/1994 | Doi et al. | |
| 5,452,367 A | 9/1995 | Bick et al. | |
| 5,531,227 A | 7/1996 | Schneider | |
| 5,537,485 A | 7/1996 | Nishikawa et al. | |
| 5,539,426 A * | 7/1996 | Nishikawa et al. | 345/635 |
| 5,568,384 A | 10/1996 | Robb et al. | |
| 5,579,471 A | 11/1996 | Barber et al. | |
| 5,586,197 A | 12/1996 | Tsujimura et al. | |

(Continued)

FOREIGN PATENT DOCUMENTS

| WO | WO 99/04680 A2 | 2/1999 |
|---|---|---|
| WO | WO 99/34319 A1 | 7/1999 |
| WO | WO 00/43910 A1 | 7/2000 |
| WO | WO 01/11489 | 2/2007 |

OTHER PUBLICATIONS

Shafer, G., Constructive probability. Synthese 48 1-60. 1981. Reprinted as Chapter 9 of Classic Works of the Dempster-Shafer Theory of Belief Functions, edited by Ronald Yager and Liping Liu, Springer 2008.

(Continued)

*Primary Examiner* — Hung T Vy
(74) *Attorney, Agent, or Firm* — Foley & Lardner LLP

(57) ABSTRACT

A computer-aided image comparison, evaluation and retrieval system compares objects and object clusters, or images. User controlled or automatic filtering to enhance object features may be performed prior to object definition/detection. The query image may be substantially continuously displayed during the image filtering and object definition processes. Scoring to suspected biological, medical, chemical, physical or clinical condition may be performed based on retrieved objects or images and their relative similarities to the unknown.

17 Claims, 10 Drawing Sheets

(56) References Cited

U.S. PATENT DOCUMENTS

| | | |
|---|---|---|
| 5,638,458 A | 6/1997 | Giger et al. |
| 5,640,462 A | 6/1997 | Sato et al. |
| 5,644,765 A | 7/1997 | Shimura et al. |
| 5,657,362 A | 8/1997 | Giger et al. |
| 5,659,626 A | 8/1997 | Ort et al. |
| 5,684,999 A | 11/1997 | Okamoto |
| 5,708,805 A | 1/1998 | Okamoto et al. |
| 5,740,267 A * | 4/1998 | Echerer et al. ............... 382/132 |
| 5,748,173 A | 5/1998 | Gur |
| 5,787,419 A | 7/1998 | Sato et al. |
| 5,802,361 A | 9/1998 | Wang et al. |
| 5,807,256 A | 9/1998 | Taguchi et al. |
| 5,819,288 A | 10/1998 | De Bonet |
| 5,832,103 A | 11/1998 | Giger et al. |
| 5,835,619 A | 11/1998 | Morimoto et al. |
| 5,852,823 A | 12/1998 | De Bonet |
| 5,857,199 A | 1/1999 | Tamano et al. |
| 5,881,124 A | 3/1999 | Giger et al. |
| 5,893,095 A | 4/1999 | Jain et al. |
| 5,906,578 A * | 5/1999 | Rajan et al. ................ 600/424 |
| 5,911,139 A | 6/1999 | Jain et al. |
| 5,919,135 A | 7/1999 | Lemelson |
| 5,930,783 A | 7/1999 | Li et al. |
| 5,931,780 A | 8/1999 | Giger et al. |
| 5,974,165 A | 10/1999 | Giger et al. |
| 5,974,201 A | 10/1999 | Chang et al. |
| 5,974,412 A * | 10/1999 | Hazlehurst et al. ................. 1/1 |
| 5,982,953 A * | 11/1999 | Yanagita et al. ............. 382/294 |
| 5,984,870 A | 11/1999 | Giger et al. |
| 5,987,094 A * | 11/1999 | Clarke et al. ................. 378/62 |
| 6,011,862 A | 1/2000 | Doi et al. |
| 6,012,069 A | 1/2000 | Shibazaki |
| 6,018,586 A | 1/2000 | Kamei |
| 6,032,157 A | 2/2000 | Tamano et al. |
| 6,032,678 A * | 3/2000 | Rottem ........................ 600/437 |
| 6,058,322 A | 5/2000 | Nishikawa et al. |
| 6,067,373 A | 5/2000 | Ishida et al. |
| 6,072,904 A | 6/2000 | Desai et al. |
| 6,088,473 A | 7/2000 | Xu et al. |
| 6,112,112 A | 8/2000 | Gilhuijs et al. |
| 6,138,045 A | 10/2000 | Kupinski et al. |
| 6,165,734 A | 12/2000 | Garini et al. |
| 6,167,146 A | 12/2000 | Rogers et al. |
| 6,181,414 B1 | 1/2001 | Raz et al. |
| 6,181,817 B1 | 1/2001 | Zabih et al. |
| 6,185,320 B1 | 2/2001 | Bick et al. |
| 6,198,838 B1 | 3/2001 | Roehrig et al. |
| 6,205,236 B1 | 3/2001 | Rogers et al. |
| 6,205,348 B1 | 3/2001 | Giger et al. |
| 6,226,636 B1 | 5/2001 | Abdel-Mottaleb et al. |
| 6,240,423 B1 | 5/2001 | Hirata |
| 6,246,804 B1 | 6/2001 | Sato et al. |
| 6,263,092 B1 | 7/2001 | Roehrig et al. |
| 6,278,793 B1 | 8/2001 | Gur et al. |
| 6,282,305 B1 | 8/2001 | Huo et al. |
| 6,282,307 B1 | 8/2001 | Armato, III et al. |
| 6,289,353 B1 * | 9/2001 | Hazlehurst et al. ................. 1/1 |
| 6,300,078 B1 | 10/2001 | Friend et al. |
| 6,301,378 B1 | 10/2001 | Karssemeijer et al. |
| 6,303,291 B1 | 10/2001 | Friend et al. |
| 6,310,967 B1 | 10/2001 | Heine et al. |
| 6,317,617 B1 | 11/2001 | Gilhuijs et al. |
| 6,335,980 B1 | 1/2002 | Armato, III et al. |
| 6,351,573 B1 | 2/2002 | Schneider |
| 6,389,157 B2 | 5/2002 | Rogers et al. |
| 6,415,048 B1 | 7/2002 | Schneider |
| 6,424,332 B1 * | 7/2002 | Powell ........................ 345/156 |
| 6,432,053 B1 | 8/2002 | Fecht et al. |
| 6,434,261 B1 | 8/2002 | Zhang et al. |
| 6,434,262 B2 | 8/2002 | Wang |
| 6,442,287 B1 | 8/2002 | Jiang et al. |
| 6,470,092 B1 | 10/2002 | Li et al. |
| 6,483,934 B2 | 11/2002 | Armato, III et al. |
| 6,491,702 B2 | 12/2002 | Heilbrun et al. |
| 6,524,246 B1 | 2/2003 | Kelly et al. |
| 6,526,168 B1 | 2/2003 | Ornes et al. |
| 6,546,137 B1 * | 4/2003 | Lai et al. ....................... 382/217 |
| 6,549,646 B1 | 4/2003 | Yeh et al. |
| 6,553,356 B1 | 4/2003 | Good et al. |
| 6,556,699 B2 | 4/2003 | Rogers et al. |
| 6,577,752 B2 | 6/2003 | Armato, III et al. |
| 6,611,766 B1 * | 8/2003 | Larsen et al. .................. 702/19 |
| 6,629,065 B1 | 9/2003 | Gadh et al. |
| 6,630,937 B2 | 10/2003 | Kallergi et al. |
| 6,650,766 B1 | 11/2003 | Rogers et al. |
| 6,654,728 B1 | 11/2003 | Li et al. |
| 6,683,973 B2 | 1/2004 | Li et al. |
| 6,690,817 B1 | 2/2004 | Cabib et al. |
| 6,707,878 B2 | 3/2004 | Claus et al. |
| 6,724,856 B2 | 4/2004 | De Man et al. |
| 6,724,925 B2 | 4/2004 | Armato, III et al. |
| 6,725,080 B2 | 4/2004 | Melkent et al. |
| 6,728,334 B1 | 4/2004 | Zhao |
| 6,733,448 B2 | 5/2004 | Kelly et al. |
| 6,738,500 B2 | 5/2004 | Bankman et al. |
| 6,748,047 B2 | 6/2004 | Gonzalez Trotter et al. |
| 6,757,415 B1 | 6/2004 | Rogers et al. |
| 6,760,468 B1 | 7/2004 | Yeh et al. |
| 6,763,128 B1 | 7/2004 | Rogers et al. |
| 6,785,410 B2 | 8/2004 | Vining et al. |
| 6,795,521 B2 | 9/2004 | Hsu et al. |
| 6,799,066 B2 | 9/2004 | Steines et al. |
| 6,801,645 B1 | 10/2004 | Collins et al. |
| 6,804,683 B1 * | 10/2004 | Matsuzaki et al. ......... 707/104.1 |
| 6,808,495 B2 | 10/2004 | Kelly et al. |
| 6,813,375 B2 | 11/2004 | Armato, III et al. |
| 6,819,785 B1 | 11/2004 | Vining et al. |
| 6,819,790 B2 | 11/2004 | Suzuki et al. |
| 6,840,239 B2 | 1/2005 | Myrman |
| 6,855,114 B2 | 2/2005 | Drukker et al. |
| 6,878,115 B2 | 4/2005 | Dione et al. |
| 6,882,700 B2 | 4/2005 | Wang et al. |
| 6,898,303 B2 | 5/2005 | Armato, III et al. |
| 6,901,156 B2 | 5/2005 | Giger et al. |
| 6,909,795 B2 | 6/2005 | Tecotzky et al. |
| 6,920,347 B2 | 7/2005 | Simon et al. |
| 6,932,768 B2 | 8/2005 | Kelly et al. |
| 6,937,776 B2 | 8/2005 | Li et al. |
| 6,941,323 B1 | 9/2005 | Galperin |
| 6,968,224 B2 | 11/2005 | Kessman et al. |
| 6,970,587 B1 | 11/2005 | Rogers |
| 6,996,549 B2 | 2/2006 | Zhang et al. |
| 6,999,549 B2 | 2/2006 | Sabol et al. |
| 7,027,642 B2 | 4/2006 | Rubbert et al. |
| 7,054,473 B1 | 5/2006 | Roehrig et al. |
| RE39,133 E | 6/2006 | Clayton et al. |
| 7,058,210 B2 | 6/2006 | Mundy et al. |
| 7,072,498 B1 | 7/2006 | Roehrig et al. |
| 7,085,400 B1 | 8/2006 | Holsing et al. |
| 7,123,762 B2 | 10/2006 | Giger et al. |
| 7,162,066 B2 * | 1/2007 | Oosawa ...................... 382/132 |
| 7,184,582 B2 | 2/2007 | Giger et al. |
| 7,272,593 B1 * | 9/2007 | Castelli et al. ............... 707/600 |
| 7,359,542 B2 * | 4/2008 | Oosawa ...................... 382/132 |
| 7,447,670 B1 | 11/2008 | Chen |
| 2001/0021264 A1 | 9/2001 | Armato, III et al. |
| 2001/0043729 A1 | 11/2001 | Giger et al. |
| 2001/0053240 A1 * | 12/2001 | Oosawa ...................... 382/128 |
| 2002/0006216 A1 | 1/2002 | Armato, III et al. |
| 2002/0009215 A1 | 1/2002 | Armato, III et al. |
| 2002/0025063 A1 | 2/2002 | Jiang et al. |
| 2002/0044691 A1 * | 4/2002 | Matsugu ...................... 382/218 |
| 2002/0090126 A1 * | 7/2002 | Oosawa ...................... 382/132 |
| 2002/0126879 A1 * | 9/2002 | Mihara et al. ................ 382/118 |
| 2002/0196966 A1 | 12/2002 | Jiang et al. |
| 2003/0013951 A1 * | 1/2003 | Stefanescu et al. ........... 600/407 |
| 2003/0053674 A1 | 3/2003 | Armato, III et al. |
| 2003/0125621 A1 | 7/2003 | Drukker et al. |
| 2003/0133601 A1 | 7/2003 | Giger et al. |
| 2003/0161513 A1 | 8/2003 | Drukker et al. |
| 2003/0174873 A1 | 9/2003 | Giger et al. |
| 2004/0077952 A1 * | 4/2004 | Rafter et al. ................. 600/481 |
| 2004/0101181 A1 | 5/2004 | Giger et al. |
| 2004/0147840 A1 * | 7/2004 | Duggirala et al. ............ 600/437 |

(56) References Cited

U.S. PATENT DOCUMENTS

| | | |
|---|---|---|
| 2004/0190763 A1 | 9/2004 | Giger et al. |
| 2004/0247166 A1 | 12/2004 | Giger et al. |
| 2004/0258310 A1 | 12/2004 | Giger et al. |
| 2005/0149360 A1 | 7/2005 | Galperin |
| 2005/0234570 A1 | 10/2005 | Horsch et al. |
| 2006/0004278 A1 | 1/2006 | Giger et al. |
| 2006/0018548 A1 | 1/2006 | Chen et al. |
| 2006/0149360 A1 | 7/2006 | Schwammenthal et al. |
| 2007/0036418 A1 | 2/2007 | Pan et al. |
| 2008/0037852 A1 | 2/2008 | Zhou et al. |

OTHER PUBLICATIONS

André, et al. 2001. Investigation of a method to assess breast ultrasound level of suspicion. *SPIE Medical Imaging*, 4322:507-512.

André, et al. 2002. Improving the accuracy of diagnostic breast ultrasound. In R. G. Maev (Ed.), *Acoustical Imaging* (vol. 26, pp. 453-460). New York: Plenum.

André, et al. 2003. ROC analysis of lesion descriptors in breast ultrasound images. *Proceedings of the SPIE* (vol. 5034, pp. 453-461).

André, et al. 2007. Diagnostic performance of a computer-aided image analysis system for breast ultrasound. In M. P. Andre (Ed.), *Acoustical Imaging* (vol. 28, pp. 341-348). Amsterdam: Springer.

André, et al. 2007. Optimization of a breast mass classifier for computer-aided ultrasound analysis. In M. P. Andre (Ed.), *Acoustical Imaging* (vol. 28, pp. 267-277). Amsterdam: Springer.

Baker, et al. 1995. Breast cancer: Prediction with artificial neural network based on BI-RADS standardized lexicon. *Radiology*, 196(3):817-822.

Baker, et al. 2004. Computer-aided detection in screening mammography: Variability in cues. *Radiology*, 233(2):411-417.

Bimbo, et al. 1998. Using weighted spatial relationships in retrieval by visual contents. In E. Vicario (Ed.), *Image Description and Retrieval*, Chap. 7, pp. 161-191.

Chen, et al. 2003. Breast lesions on sonograms: Computer-aided diagnosis with nearly setting-independent features and artificial neural networks. *Radiology*, 226(2):504-514.

Drukker, et al. 2005. Robustness of computerized lesion detection and classification scheme across different breast US platforms. *Radiology*, 237(3):834-840.

Flickner, et al. 1995. Query by image and video content: The QBIC system. *Computer*, 28(9):23-32.

Galperin, M. 2003. Statistical analysis to assess automated level of suspicion scoring methods in breast ultrasound. *Proceedings of the SPIE* (vol. 5034, pp. 495-502).

Galperin, M. 2005. Application of parametric statistical weights in CAD imaging systems. *Proceedings of the SPIE* (vol. 5749, pp. 338-347).

Giordan, et al. 1998. Using Adobe Photoshop 5. *Que Publisher*, 600 pp.

Hirata, et al. 1993. Media based navigation for hypermedia system. *Proceedings of the Fifth ACM Conference on Hypertext*, pp. 159-173.

Hirata, et al. 1997. Object based navigation: An intuitive navigation style for content-oriented integration environment. *Proceedings of the Eighth ACM Conference on Hypertext*, pp. 75-86.

Hong, et al. 2005. BI-RADS for sonography: Positive and negative predictive values of sonographic features. *AJR*, 184:1260-1265.

Huo, et al. 2002. Breast cancer: Effectiveness of computer-aided diagnosis—observer study with independent database of mammograms. *Radiology*, 224(2):560-568.

Kolb, et al. 2002. Comparison of the performance of screening mammography, physical examination, and breast US and evaluation of factors that influence them: An analysis of 27,825 patient evaluations. *Radiology*, 225(1):165-175.

Lee, et al. 1994. Query by image content using multiple object and multiple features: User interface issues. *Image Processing*, 2:76-80.

Malur, et al. 2001. Comparison of written reports of mammography, sonography and magnetic resonance mammography for preoperative evaluation of breast lesions, with special emphasis on magnetic resonance mammography. *Breast Cancer Research*, 3(1):55-60.

Markey, et al. 2002. Differences between computer-aided diagnosis of breast masses and that of calcifications. *Radiology*, 223(2):489-493.

Patel, et al. 2001. Comparison of three-class classification performance metrics: A case study in breast cancer CAD. *Medical Decision Making*, 21(5):409-417.

Stavros, et al. 1995. Solid breast nodules: Use of sonography to distinguish between benign and malignant lesions. *Radiology*, 196(1):123-134.

US Office Action on dated Dec. 19, 2013 for U.S. Appl. No. 11/859,311.

\* cited by examiner

OBJECT BASED IMAGE RETRIEVAL

This application is a continuation of U.S. Ser. No. 11/007,062, filed Dec. 7, 2004, now U.S. Pat. No. 7,483,919 which is a continuation-in-part of U.S. application Ser. No. 09/370,366 filed Aug. 9, 1999, now U.S. Pat. No. 6,941,323. Both of these applications are hereby incorporated by reference in their entireties.

BACKGROUND OF THE INVENTION

1. Field of the Invention

The invention relates to management of an image database and the retrieval of images therefrom.

2. Description of the Related Technology

The ability to search image databases and retrieve images therefrom with desired features or characteristics is important in many different environments. However, as a collection of images to be searched grows in size, the ability to search and evaluate the collection manually for images having the desired features becomes increasingly limited. It can be appreciated that huge image databases of thousands or even millions of images have been created which are essentially impossible to search and evaluate manually.

Several approaches have been used to automate the image search process. In some cases, images are digitized and stored in a database in association with one or more keywords which describe their content or character. Such a database can be searched linguistically for particular keywords, and images which are associated with these keywords are retrieved in response.

In a more recently developed alternative method, one or more "query images" are utilized, and images from the database which are in some sense similar to the query image are located and retrieved. In these systems, the pixel values of the query image and the images in the database are processed to produce a set of parameters indicative of color distribution, pixel intensity variation across the image, as well as other characteristics of the image as a whole. These parameters are calculated using various image filtering and processing techniques so as to produce a vector of feature parameters which is indicative of the image itself. The comparison process involves comparing feature vectors from images in the database with a query feature vector, and images from the database having similar feature vectors are retrieved. A system of this nature is described in U.S. Pat. No. 5,644,765 to Shimura et al., the disclosure of which is hereby incorporated by reference in its entirety.

The above described systems have several limitations. The most serious drawback for both cases is that image content is inadequately defined, which impacts both system recall and precision. Recall is the proportion of relevant images in the database that are retrieved, and precision is the proportion of retrieved documents that are actually relevant. These two measures may be traded off one for the other, and the goal of image retrieval is to maximize them both.

SUMMARY

The invention comprises methods and systems for processing, comparing and retrieving images. In one embodiment, the invention comprises a method of identifying similarities between first and second imaged structures present in one or more digital images. The method includes processing one or more digital images so as to define at least first and second objects, assigning a first object characterization parameter set to the first object, and assigning a second object characterization parameter set to the second object. The method further comprises calculating a similarity index based on the first object characterization parameter set and the second object characterization parameter set.

Scoring to suspected biological, medical, chemical, physical or clinical condition may be performed based on retrieved objects or images and their relative similarities to the unknown.

DETAILED DESCRIPTION OF THE INVENTION

Embodiments of the invention will now be described with reference to the accompanying Figures, wherein like numerals refer to like elements throughout. The terminology used in the description presented herein is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

In many imaging applications, a user of the system wishes to find images in an image database which contain a certain defined object. In some cases, the search may be for images containing a chair, sunset, mountain, or the like. This may be the case in the advertising or commercial arts fields, for example, where large searchable image files are kept for use in the production of artwork, posters, etc. Other applications may also benefit from a robust object recognition system. In the health care environment, images such as X-ray films, CAT scans, ultrasound and MRI images generally contain specific internal objects of interest such as blocked blood vessels, tumors, malignant or benign growth and other structures. In many cases, diagnosis and treatment would be facilitated if a physician could search and evaluate an image database for similar structures found in other patients so as to obtain valuable information regarding diagnosis, treatment, and outcome for other patients showing similar objects under X-ray or MRI imaging. As yet another example, geographical and geological surveying, mapping, and other forms of reconnaissance (including military targeting systems) would also be facilitated by such a system. Structures in aerial and satellite photographs could more easily be correlated to specific physical objects if specific ambiguous structures in the image could be cross referenced to structures found in other aerial or satellite photographs. To address this need, embodiments of the invention allow a user to focus image database searching and evaluation on objects contained in an image. This dramatically improves the ability of the system to quickly and accurately identify desired images over the methods currently available in the technology and industry.

Figure 1:
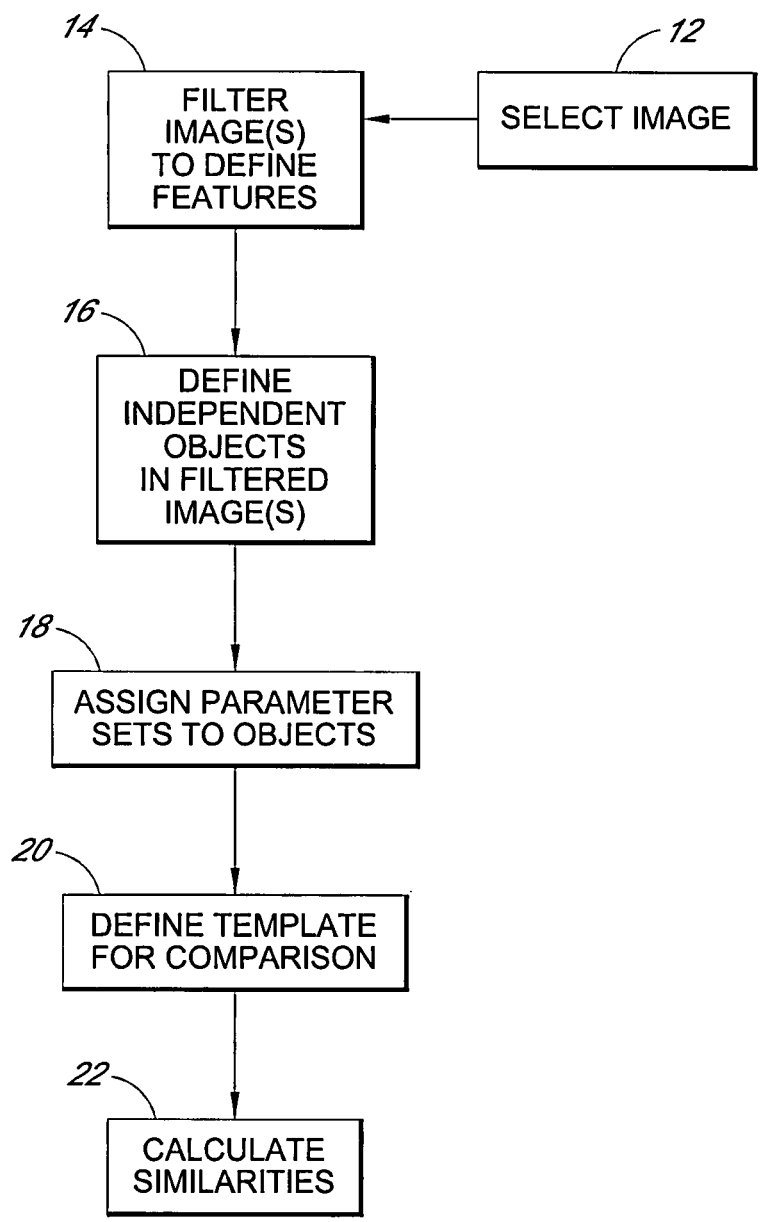
FIG. 1 is a flowchart of a method of image retrieval in one embodiment of the invention.

Referring now to the flowchart of FIG. 1, a method of image comparison according to one embodiment of the method begins at block 12, where a starting or query image is selected. The query image will typically be provided by a user of the system and will comprise an image which contains one or more structures or objects of interest. Initially, the structure of interest in the image may not be well defined or distinct relative to the background. For example, the object boundaries may be poorly delineated, or it may have significant internal features present that are not immediately apparent in the image.

To help define the object of interest, both in terms of its boundaries and its internal features, the system performs image filtering at block 14. In advantageous embodiments, the filtering performed is under the control of the system user. The system may also perform filtering automatically using default filter functions or filter functions previously defined and stored by a user. A wide variety of well known image filtering techniques may be made available to the user. Many image filtering techniques which may be used in embodiments of the invention are described at pages 151-346 of *The Image Processing Handbook,* 2d Edition, John C. Russ, author, and published in 1995 by CRC Press, which is hereby incorporated by reference into this application in its entirety. Several filters which are utilized in one embodiment of the invention are set forth below with reference to FIGS. 4-6. These filters may enhance edges, enhance the appearance of pixels in particular brightness ranges, stretch contrast in selected pixel brightness ranges, reduce noise, or perform any of a wide variety of pixel processing functions. It will be appreciated that the filtering performed at block 14 may comprise the sequential application of several individual pixel filtering functions. Advantageously, filtering performed in block 14 can result in the enhancement of features which are characteristic of objects of interest or objects within a certain class, etc., but which do not appear in other objects or in the image background.

Following the filtering of block 14, objects within the filtered image are defined at block 16. Once again, this process may be performed under the control of the user, or performed automatically by the system. In general, this process involves evaluating pixel values so as to classify them as either an object pixel or a background pixel. As with the filtering performed at block 14, the object definition process of block 16 may be done using many well known techniques, some of which are described at pages 347-405 of *The Image Processing Handbook* mentioned above. Example object definition protocols provided in one embodiment of the invention are described in more detail with reference to FIG. 7.

Next, at block 18, each defined object is separately numerically characterized by a set of parameters which are calculated from the pixel locations and brightness values of each defined object. In general, the numerical parameters are measures of the object's shape, size, brightness, texture, color, and other calculated characteristics. Preferably, the values present in the parameter sets are similar for objects of the same type. Example parameters which may advantageously be used in embodiments of the invention are described below with reference to FIG. 3.

Referring now to block 20, a template for comparison is defined by the user. The template may be a single defined object, or may be a group or cluster of defined objects in a region of the image. At block 22, similarities between the template and other objects or sets of objects are calculated. If the template is a single object, this may be done by comparing the parameter set assigned to the template object with the parameter sets assigned to other objects. There are several well known ways of evaluating the similarity between two parameter vectors. For example, Euclidean or Minkowski line metrics may be used. If the parameter set is represented as a bit string, the Hamming distance may be used as the similarity measure.

In certain embodiments of the invention, multi-dimensional non-binary parameter sets are associated with the objects, and as stated above, a comparison may be performed between not only individual parameter sets but also between parameter set groups associated with clusters of a plurality of objects. In this case, more complicated formulae have been developed and may be used, based on ideas set forth in Voronin, Yu. A., *Theory of Classification and Its Applications* 1985, published in Russia by Nauka. These formulae are set forth fully below. As is also explained below, if the template comprises a set of two or more objects, the comparison involves not only a comparison of the objects themselves, but also the spatial relationship between them. This method for numeric estimation of spatial relations between objects was developed by the inventors.

It will be appreciated that accuracy in identifying similar objects is improved when the filtering and object definition steps described above result in the enhancement of object features which are associated with objects of the desired class but not associated with objects not in the desired class. These enhanced features will manifest themselves as a numerically discriminable part of the parameter set, and the parameter set may thus be utilized to differentiate objects in the desired class from objects outside the desired class. Such differentiation manifested by the system using object border contour displays. The system may use different colors of the object border contours—blue for objects touching the image edges, green—for allowed non-border objects, red—for objects filtered out by the system based on user set parameters intervals, and yellow—for template objects.

As one specific example, a query image may comprise a digital image of an area of skin pigmentation. A physician may be interested in evaluating the likelihood that the pigmentation in the image is a melanoma. Using a method according to the present invention, the digital image is filtered and an image area associated with the pigmentation is defined as an object within the image. Other images of skin pigmentation which are stored in an image database are also filtered and areas of skin pigmentation are defined as objects, advantageously using the same filters and object definition functions. These objects in the database are then also parameterized. The query parameter set is compared to the parameter sets associated with the database objects, and images of skin pigmentation which are similar are identified. Advantageously, the pigmentation area of the stored images have been previously characterized (diagnosed) as being melanoma or not. If retrieved similar object images are predominantly images of melanomas, the physician may be alerted that the possibility of melanoma for the query image is high. As mentioned above, it is advantageous if the filtering and object definition procedures enhance those aspects of skin pigmentation images which are closely associated with the presence of a melanoma. Furthermore, the parameter set itself may be tailored to the class of objects being analyzed. This may be done by assigning different weights to the different parameters of the parameter set during the comparison. For the melanoma example, a high weight may be assigned to parameters which are indicative of an irregular boundary or surface, while a lower weight may be assigned to a parameter associated with the total area of the object.

Figure 2:
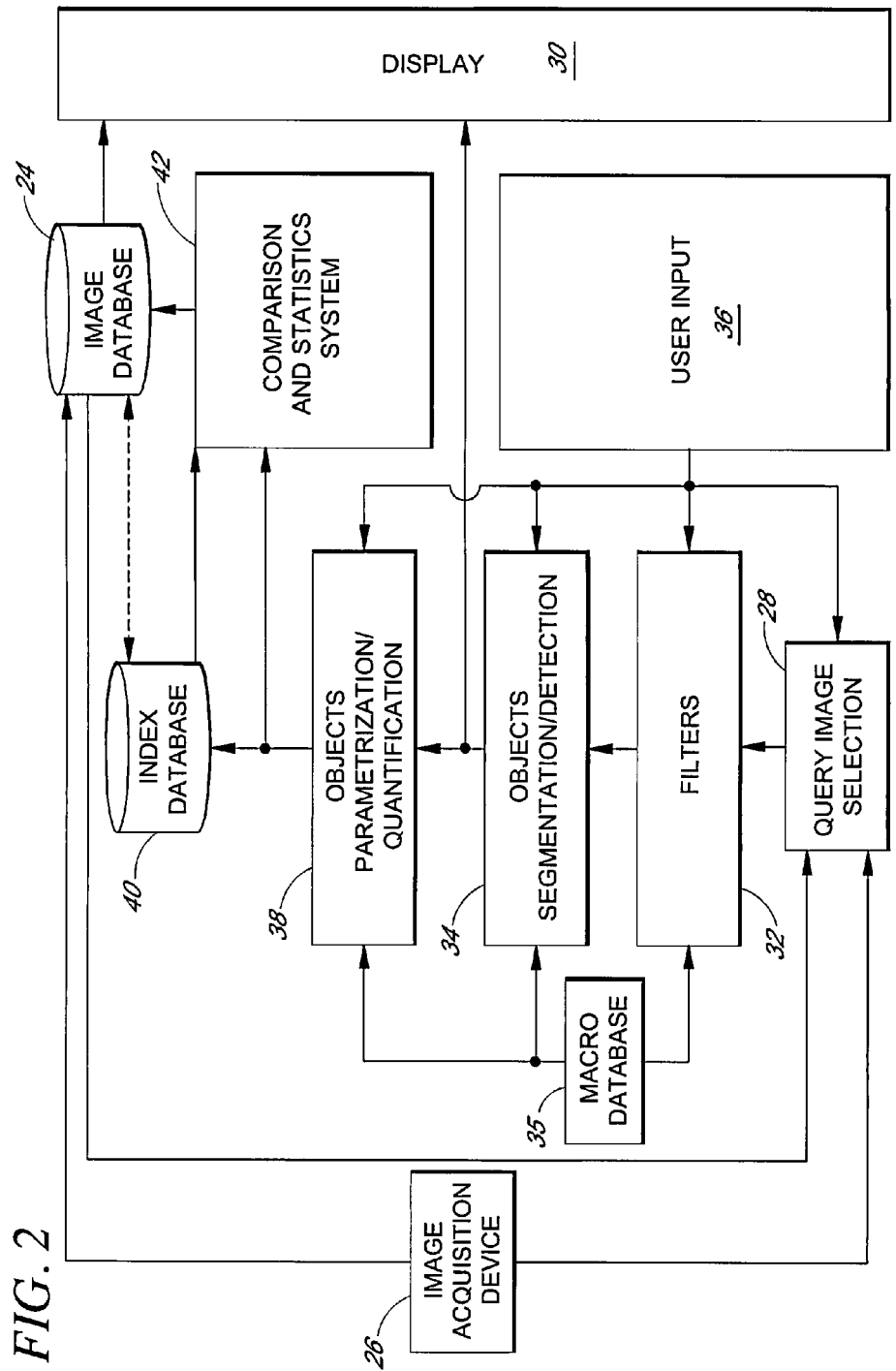
FIG. 2 is a block diagram of an image retrieval system according to the invention which may be utilized to carry out the method of FIG. 1.

A system which may be used in one embodiment of the invention is illustrated in FIG. 2. An image acquisition device 26 is used to initially create images for storage in an image database 24 and/or for routing to a query image selection module 28 of the system. The image acquisition device may be a source of images of any type, including photographs, ultrasound images, X-ray or MRI images, a CRT display or trace, or any other data source having an output, which is definable as a collection of digital values. The image acquisition device may, for example, be a digital camera. The image acquisition device may produce the image directly. The system may also import previously created images from one or more imaging sources. The image acquisition device may be an external digital imaging source for such systems like PACS, RIS, LIS or the Internet or Telnet, for example. Typically, of course, the image data array processed by the system could be a two-dimensional array of pixels wherein each pixel is assigned an associated scalar or vector value. It is also well known that a two-dimensional array of pixels may be derived from a real 3D object that was represented by 2-dimensional "slices" or scans. For grey scale images, each pixel is associated with a brightness value, typically eight bits, defining a gray scale from zero (black) to 255 (white). For color images, a three component vector of data values may be associated with each pixel. The query image selection module, may, under the control of a user, select a query image from the image acquisition device, or may retrieve an image from the image database 24.

The system also comprises a display 30 which provides a visual output of one or more images to the user of the system. For example, the query image itself will typically be displayed to the user with the display device 30. This display of the query image may further be performed after image filtering by the filter module 32 and object definition by the object definition module 34. If no filtering or object segmentation has yet been implemented by the user with these modules, the unprocessed query image will be displayed to the user.

With a user input device 36 such as a keyboard, touchpad, or mouse, the user may control the filter module 32 so as to implement the filtering described above with reference to block 14 of FIG. 1. It is one aspect of some embodiments of the invention that the image continues to be displayed as the filtering is implemented. Thus, as the user modifies the filter function being performed by the filter module 32, the visual impact of the filter application on the image is displayed to the user.

The user may also control the implementation of object definition by the object definition module 34. Pixel brightness thresholds and other features of the object definition procedure may be modified by the user with the input device 36. As with the filtering operation, the image may be displayed after object definition so that the user can observe visually the contours and internal features of objects defined in the image. If the object definition technique is modified by the user, the display of the image may be accordingly updated so that the user can evaluate the effects of the filtering alterations and image object changes graphically on the display.

In some embodiments, the user may allow the system to perform object definition automatically, without requiring any additional user input. Of course, the above described display updates may be performed after this automatic object definition as well. As is also illustrated in this Figure and is explained further below with reference to FIG. 4, the user may also control aspects of parameter calculation via the user input device 36.

It will also be appreciated that in many applications, multiple images having similar sources and structures will be processed by the user in the same way ("batch processing"). For example, cranial X-ray images may all be processed with the same filter set and object definition functions prior to parameterization—in batch. This helps ensure that compatible images and objects therein are parameterized for comparison. Of course, care must be taken that the sources of the images are themselves compatible. Overall brightness, dimensional variations, and other differences between, for example, different microscopes used to obtain the query image and images in the database 24 should be compensated for either prior to or as part of the processing procedures, known as dimension and/or brightness calibration.

To facilitate this common processing of multiple images user defined macros of filter and object definition and detection functions may be stored in a macro database 35 for future use on additional images. The user-friendliness of the system is improved by this feature because images from similar sources can be processed in the same way without requiring the user to remember and manually re-select the same set of filtering and object definition functions when processing similar images in the future. In one embodiment, the user may operate on an image using either individual filter and object definition functions stored in the macro database or user defined groups of individual filter and object definition functions stored in the macro database 35.

The object definition module 34 is connected to an object parameterization module 38, which receives the pixel values and contour coordinates of the objects defined in the image. This module then calculates the parameter sets described above with reference to block 18 of FIG. 1 using the input pixel values. The calculated parameter sets may be stored in an index database 40 for future use. During the image searching, evaluating and retrieval process, one or more parameter sets associated with a template will be forwarded to a parameter set comparison module 42 along with parameter sets associated with other objects in the image or other objects in images stored in the image database 24. Objects or object clusters that are similar to the template, are then also displayed to the user on the display 30.

Figure 3:
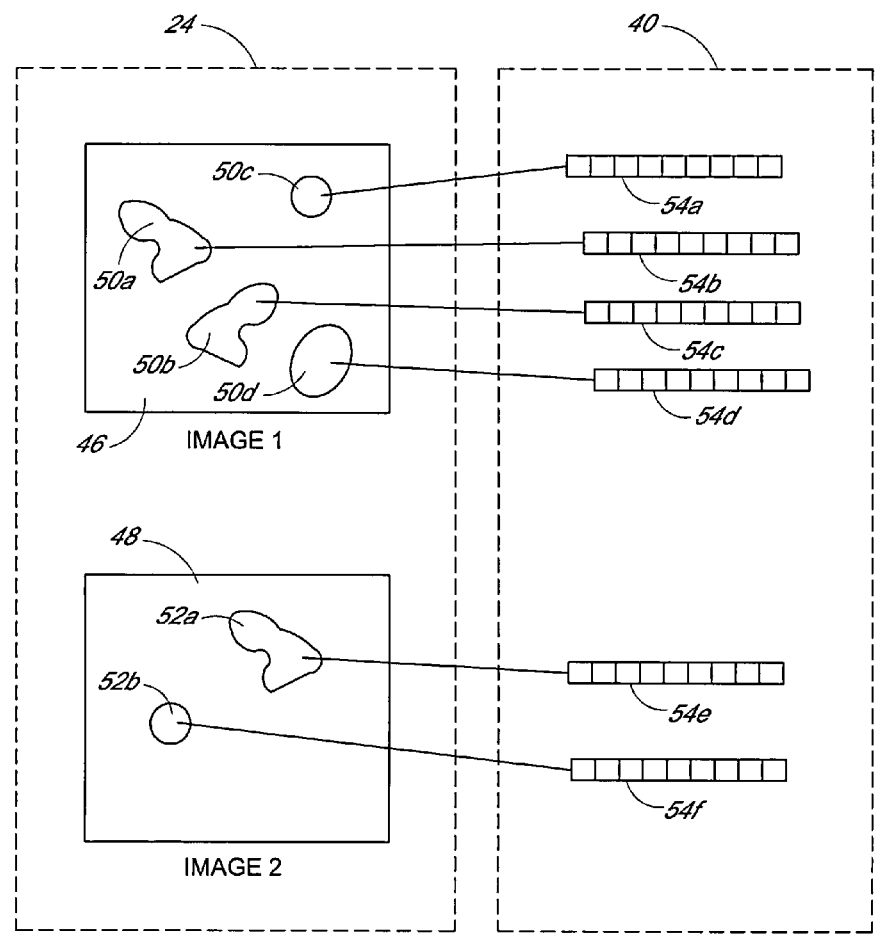
FIG. 3 is a conceptual schematic of parameter sets associated with objects segmented from an image which may be created by the object parameterzation module of FIG. 2.

Referring now to FIG. 3, it is one aspect of the invention that any given image may have associated with it several different parameter sets, with each parameter set associated with a detected object in that image. Thus, the image database 24 may store a plurality of images 46, 48, each of which includes a plurality of defined objects 50a-d and 52a-b. Each object is associated with a parameter set 54a-f, which is stored in the index database 40.

In one embodiment, the parameter set includes a computation of the object area by a formula which counts the number of pixels defined as part of object "A" and multiplies that number by a calibration coefficient as follows:

$$\sum_{i,j} z * \delta_{ij}, \delta_{ij} = \begin{cases} 1, ij \in A \\ 0, ij \notin A \end{cases}, \quad (1)$$

where z is a user defined dimensional calibration coefficient.

When the object has many internal holes, the area parameter may be calculated instead by the formula:

$$\frac{\sum_i (X_i + X_{i-1}) * (Y_i - Y_{i-1})}{2}, \quad (2)$$

wherein X, Y are the coordinates of the periphery pixels of the object.

Other advantageous object characterization parameters include the length of the perimeter, and the maximum and minimum diameters of the object through the center of gravity of the object. These may be calculated with the formulas:

$$\sum_i \sqrt{(X_i - X_{i-1})^2 + (Y_i - Y_{i-1})^2} \quad (3)$$

for perimeter, $$4 * \sqrt{\frac{\overline{x^2} - (\overline{x})^2 + \overline{y^2} - (\overline{y})^2 + \sqrt{(\overline{x^2} - (\overline{x})^2 - \overline{y^2} + (\overline{y})^2)^2 + 4*(\overline{xy} - \overline{x}*\overline{y})^2}}{2}}, \quad (4)$$

for maximum diameter, and $$4 * \sqrt{\frac{\overline{x^2} - (\overline{x})^2 + \overline{y^2} - (\overline{y})^2 - \sqrt{(\overline{x^2} - (\overline{x})^2 - \overline{y^2} + (\overline{y})^2)^2 + 4*(\overline{xy} - \overline{x}*\overline{y})^2}}{2}}, \quad (5)$$

for minimum diameter, where $$\overline{x} = \left(\sum_{j,i \in A} X_{ij}\right) \bigg/ \left(\sum_{j,i \in A} \delta_{ij}\right), \overline{y} = \left(\sum_{j,i \in A} Y_{ij}\right) \bigg/ \left(\sum_{j,i \in A} \delta_{ij}\right),$$

$$\overline{x^2} = \left(\sum_{j,i \in A} X_{ij}^2\right) \bigg/ \left(\sum_{j,i \in A} \delta_{ij}\right), \overline{y^2} = \left(\sum_{j,i \in A} Y_{ij}^2\right) \bigg/ \left(\sum_{j,i \in A} \delta_{ij}\right),$$

$$\overline{xy} = \left(\sum_{j,i \in A} X_{ij}*Y_{ij}\right) \bigg/ \left(\sum_{j,i \in A} \delta_{ij}\right)$$

Other shape and size related parameters may be defined and included in the parameter set, such as form factor:

$$\frac{4*\pi*\text{Area}}{(\text{Perimeter})^2} \quad (6)$$

equivalent circular diameter:

$$\sqrt{\frac{4*\text{Area}}{\pi}} \quad (7)$$

and aspect ratio, which represents the ratio of the maximum diameter and minimum diameters through the center of gravity. The maximum and minimum Ferret diameters of the object may also be included as part of the parameter set, namely:

max $X_{ij}$–min $X_{ij}$; max $Y_{ij}$–min $Y_{ij}$, where $$i,j \in A \quad (8)$$

Parameters which relate to pixel intensities within the object are also advantageous to include in the object characterization parameter set. These may include optical density, which may be calculated as:

$$-\log_{10}\left(\frac{\sum_{ij \in A} I_{ij}}{\sum_{ij \in A} \delta_{ij}} \bigg/ I_{max}\right) \quad (9)$$

and integrated density:

$$\sum_{i,j \in A} I_{ij} \quad (10)$$

where $I_{ij}$ is the brightness (i.e. 0-255 for 8-bit images or 0-65536 for 16-bit images or 0-16777216 for 24-bit images) of pixel ij, and $I_{max}$ is the maximum pixel brightness in the area/image.

More complicated intensity functions which parameterize the texture of the object may be utilized as well. One such parameter is a relief parameter which may be calculated as:

$$\sum_{i,i \in A; Nij \geq 2} rl_{ij} \bigg/ \sum_{i,j \in A; Nij \geq} \delta_{ij}, \quad (11)$$

where $$rl_{ij} = r_{ij} * \Omega(Nij);$$

where $\Omega(N_{ij})$ is a function of $N_{ij}$ $$r_{ij} = \left(\sum_{m=i-1}^{i+1} \sum_{n=j-1}^{j+1} \text{abs}(I_{nm} - I_{ij})\right) \bigg/ N_{ij};$$

$n, m \in A;$ $$N_{ij} = \sum_{n=i-1}^{i+1} \sum_{m=j-1}^{j+1} \delta_{nm}$$

This parameter belongs to a textural class of parameters and is a measure of the average difference between a pixel values in the object and the values of its surrounding pixels. In the simplest case, $\Omega(N_{ij})=N_{ij}$, although the function may comprise multiplication by a constant, or may involve a more complicated function of the number of nearest neighbors or pixel position within the object.

Other examples include homogeneity:

$$\Phi = \sum_{Ii}\sum_{Ij}(N_{ij}/\overline{N}(DiameterFerret_{xy}))^2, \quad (12)$$

where I is intensity; i, j ∈ A; and $\overline{N}$ is a renormalizing constant and contrast:

$$L = \sum_{Ii-Ij=0}(I_i-I_j)^2 \Big[\sum_{Ii=Ij}(N_{ij}/\overline{N}(DiameterFerret_{xy}))\Big], \quad (13)$$

where I is intensity; i, j ∈ A; and $\overline{N}$ is a renormalizing constant

It will be appreciated that the nature of the parameter set may vary widely for different embodiments of the invention, and may include alternative or additional parameters not described above. The parameters set forth above, however, have been found suitable for object characterization in many useful applications.

Figure 4:
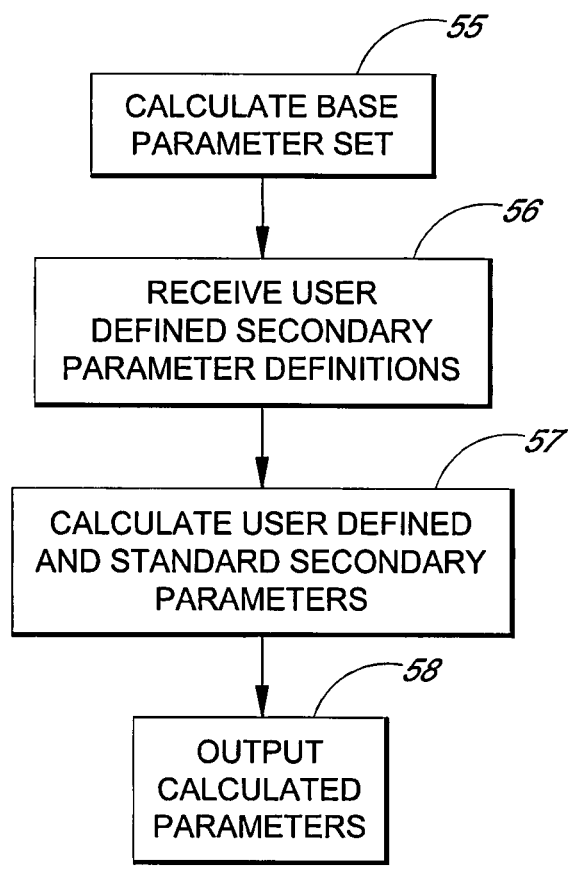
FIG. 4 is a flowchart of one embodiment of an object parameterization process which may be implemented in the object parameterization module of FIG. 2.

FIG. 4 illustrates a flowchart of the parameter set generation process which may be performed by the object paramterization module 38 of FIG. 2. Initially, at block 55, the base or fundamental parameters are calculated. These are the parameters that use raw pixel positions or intensities as inputs. Examples include area (Equation 1), perimeter (Equation 3), integrated intensity (Equation 10), etc. Another set of parameters, referred to herein as "secondary" parameters are also calculated. These are parameters which are functions of the base parameters, and which do not require any additional pixel specific information for their calculation. Examples of standard secondary parameters include Formfactor (Equation 6) and aspect ratio. In some embodiments, the user is allowed to define additional secondary parameters for object characterization which may have significance in certain image analysis applications. For example, a new hypothetical parameter comprising the ratio of Formfactor to Area may be defined and made part of the object characterization parameter set. Thus, at block 56, the system may receive user input (by entering information into a dialog box with a mouse and/or keyboard, for example) regarding secondary parameter definitions not already utilized by the system.

At block 57 the system calculates both the user defined and standard secondary parameters, and at block 58 the parameters thus calculated are formatted into a feature vector and output to either or both the index database 40 and the comparison and statistics system 42 of FIG. 2.

In FIGS. 5 through 9, a specific implementation of the invention is illustrated by example screen displays which illustrate aspects of user control (via the input devices 36 of FIG. 2) and visualization (via the display 30 of FIG. 2) of the filtering and object definition processes. As will be apparent to those of skill in the art, this embodiment of the invention is implemented in software on a general purpose computer. A wide variety of data processing system environments may be utilized in conjunction with the present invention. In many embodiments, the invention is implemented in software coded in C/C++ programming languages and running on a Pentium series personal computer with, for example, as little as 128 Mbytes of RAM and a 640 MB hard drive. The personal computer in this implementation will typically be connected to an image database through a local or wide area network, or via PACS, RIS, LIS or Internet/Telnet client-server system. In another implementation, the personal computer runs a standard web browser, which display a communicating application and accesses image databases and image analysis and computer-aided detection software hosted on a remote Internet server. Intranet version of the application is also envisioned and implemented. In such case the system works as a part of PACS, for example, using LAN and HIS as a hosting system.

Figure 5:
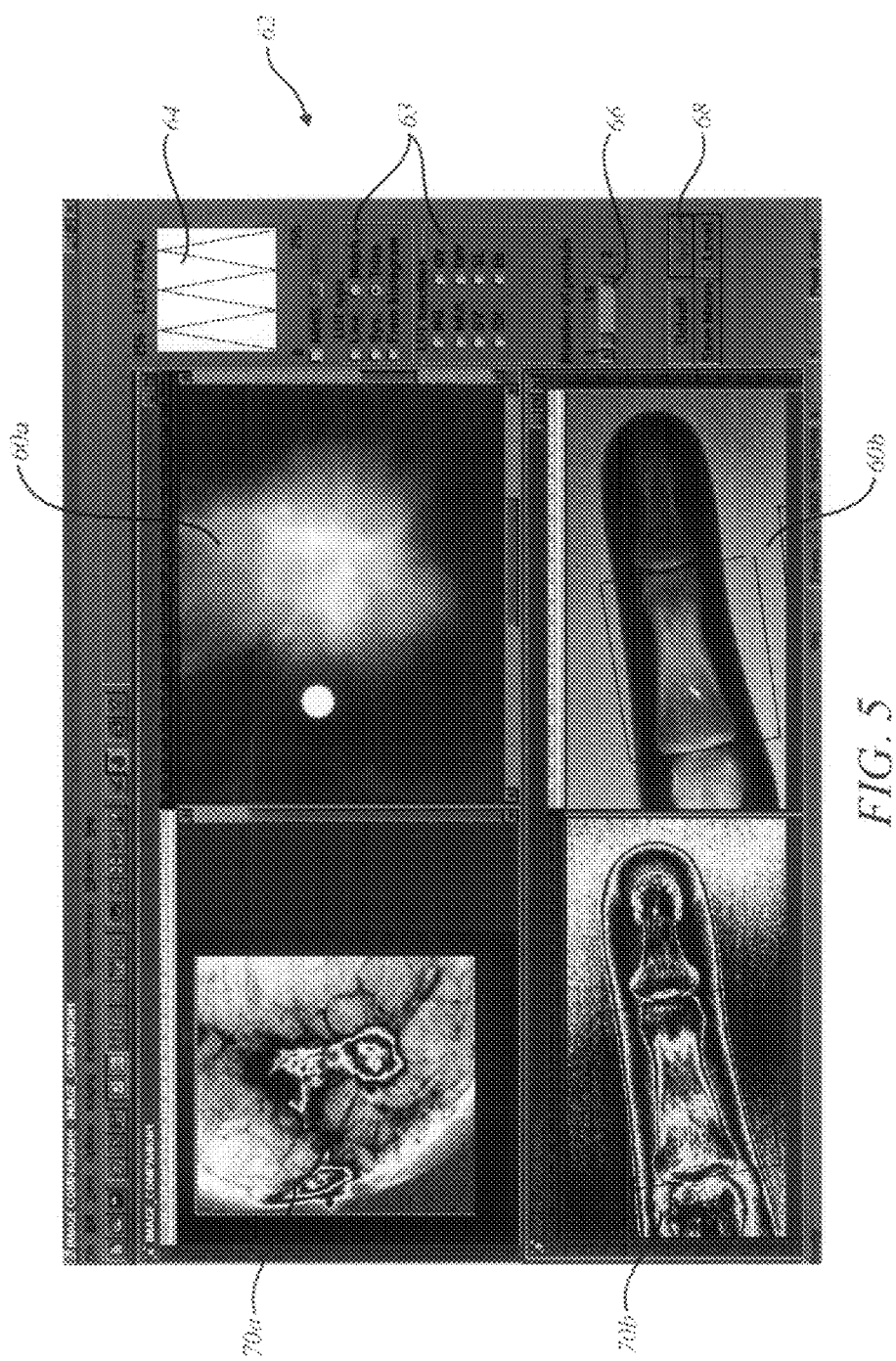
FIG. 5 is a screen display of user configured look up table filter functions according to one embodiment of the invention and which may be generated by the system of FIG. 2.

Referring now to FIG. 5, original images 60a and 60b are displayed to the user of the system in respective portions of the display. The upper display 60a comprises a close up of a suspected malignancy in a mammogram. The lower display 60b is a bone density image utilized in evaluating osteoporosis. On another portion 62 of the screen is a display of a filter protocol. This portion 62 of the screen display shown one of the computationally simplest filtering techniques under user control in this embodiment, which is look-up-table (LUT) filtering. With this filter, each input pixel brightness value is mapped onto an output pixel brightness value. If pixel brightness ranges from a value of 0 (black) to 255 (white), each value from 0 to 255 is mapped to a new value defined by the LUT being used.

In this embodiment, the user is provided with a visual indication 64 of the look-up table form being applied, with input pixel values on the horizontal axis and output pixel values on the vertical axis. Using user selectable check boxes 63, the user may define the nature of the look-up-table filter being applied. In this embodiment, the user may define both a table form and a table function. The form may be selected between linear (no effect on pixel values), triangular, and sawtooth (also referred to as notch). The triangular form is illustrated in FIG. 5. For the triangular and sawtooth forms, the user may be provided with a slidebar 66 or other input method for selecting the number of periods in the input brightness range. The user may also import a previously used user defined LUT if desired.

The look-up-table form may also be varied by additional user defined functions. These functions may include negative inversion, multiplication or division by a constant, binarization, brightness shifting, contrast stretching, and the like. For each of these functions, the user may control via slidebars or other user manipulatable displays the constants and thresholds utilized by the system for these functions. Histogram based look-up table filtering may also be provided, such as histogram equalization and histogram based piecewise contrast stretching. After the user defines the desired LUT filter, they may apply it to the image by selecting the "APPLY" button 68. The look-up-table defined by the user is then applied to the image or a selected portion thereof.

Furthermore, second display 70a and 70b of the image is provided following application of the three period triangular LUT filter. If the user modifies the LUT filter function, the image display 70a, 70b is updated to show the visual result of the new filter function when the user clicks the APPLY button 68. Thus, the user may view a substantially continuously updated filtered image as the filter functions used are modified. In filtered image 70a, regions of suspected malignancy are enhanced with respect to the background following LUT application. In the filtered image 70b, the bone density variations present in the central bone segment are enhanced and pronounced.

Figure 6:
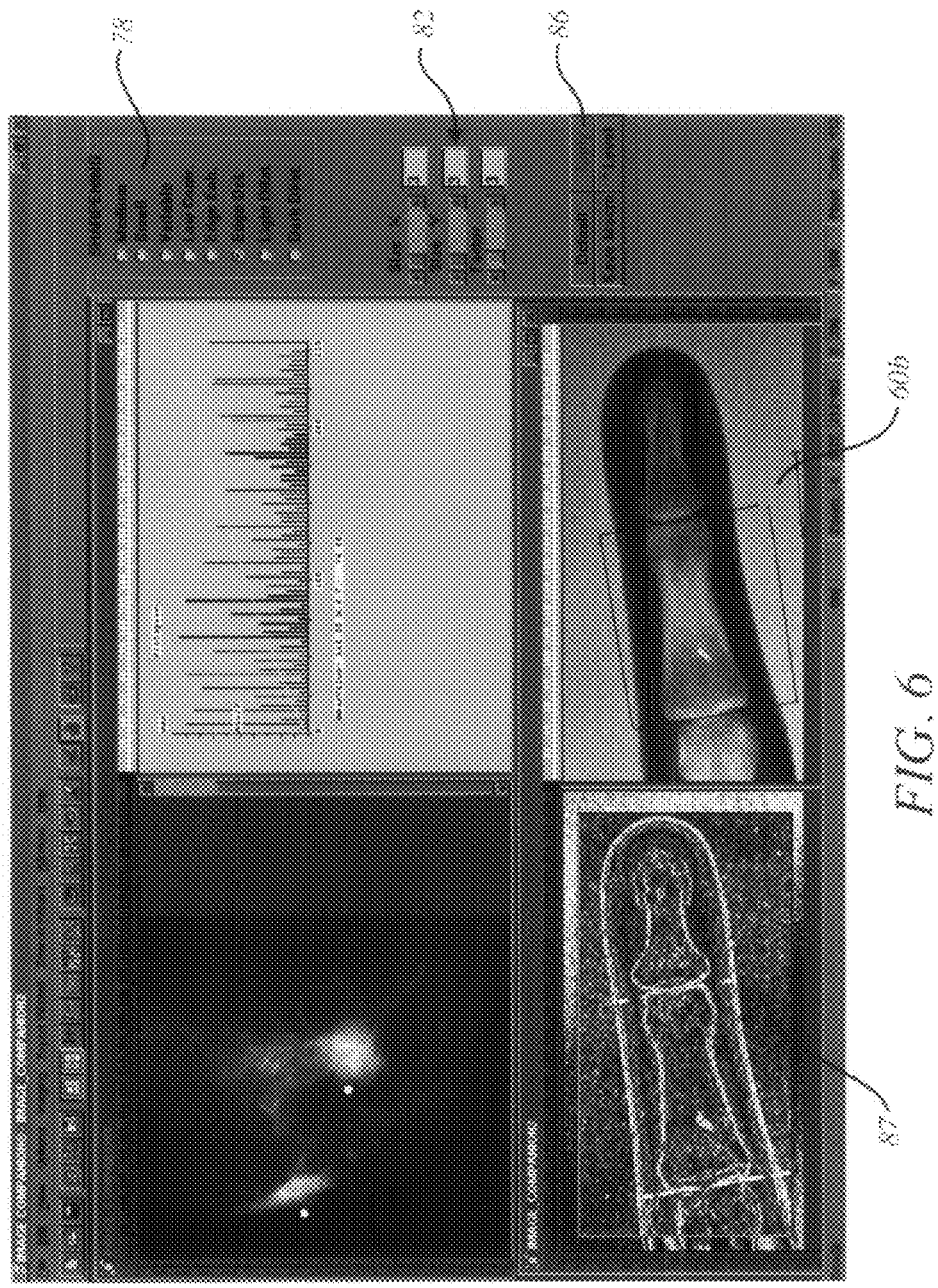
FIG. 6 is a screen display of user configured sharpening filter functions according to one embodiment of the invention and which may be generated by the system of FIG. 2.
Figure 7:
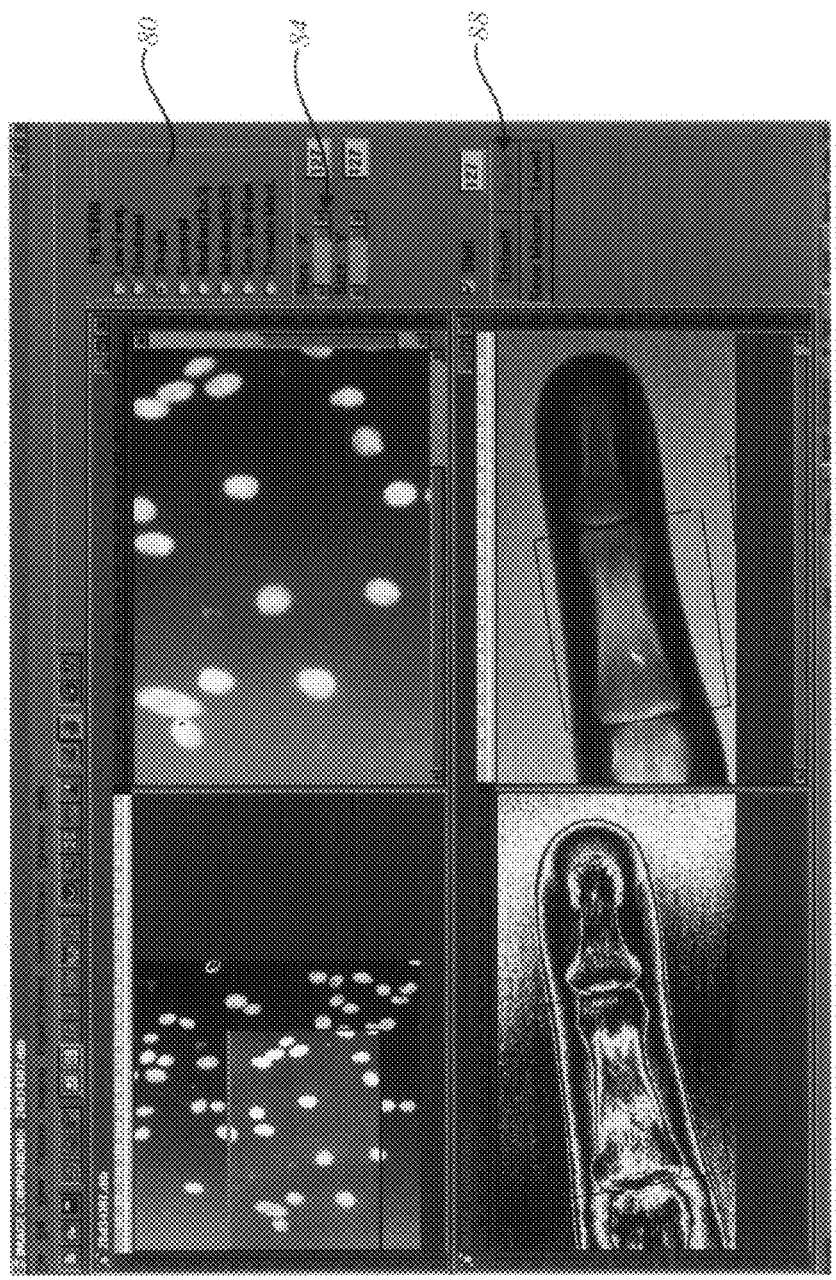
FIG. 7 is a screen display of user configured general and edge enhancement filter functions according to one embodiment of the invention and which may be generated by the system of FIG. 2.

In addition to LUT filtering, convolution filters, frequency domain filters, and other filter types may be utilized to further enhance and define significant features of imaged objects. Several specific examples provided in one embodiment of the invention are illustrated in FIGS. 6 and 7. In analogy with the user interface for the LUT filtering described with reference to FIG. 5, additional filter types may be selected with checkboxes 78, 80. Filter parameters such as filter box size are user controllable via slidebars 82, 84. APPLY buttons 86, 88 initiate the filter operation and display update to show the filtered image or image region. In FIG. 6, the bone image 60b is filtered with a 3×3 edge detection filter which produces the filtered image 87 having enhanced pixels along edges in the image. In FIG. 7, a region of interest 89 in an image of blood cells in bodily fluids where a shading filter was used to compensate for a background brightness variation across the image.

In the specific implementation illustrated in FIGS. 6 and 7, the following base set filter functions may be applied by the system user:

1. Sharpening of Small Size Details on Image

This type of filter belongs to a class of Laplacian filters. The filter is a linear filter in the frequency domain. The 3×3 kernel is understood to mean that central pixel brightness value is multiplied by 4. As a result of this filtering, the sharpness of small details (not to exceed 3×3) of the image is increased.

$$C_{mn} = \begin{Bmatrix} -1 & -1 & -1 \\ -1 & 9 & -1 \\ -1 & -1 & -1 \end{Bmatrix}$$

2. Sharpening of Middle Size Details on Image

This type of filter belongs to a class of Laplacian filters. Functionality is similar to the 3×3 kernel type filter. As a result of this filtering, the sharpness of small details (not to exceed 5×5) of the image is increased.

$$C_{mn} = \begin{Bmatrix} -1/12 & -1/12 & -2/12 & -1/12 & -1/12 \\ -1/12 & -2/12 & 3/12 & -2/12 & -1/12 \\ -2/12 & 3/12 & 28/12 & 3/12 & -2/12 \\ -1/12 & -2/12 & 3/12 & -2/12 & -1/12 \\ -1/12 & -1/12 & -2/12 & -1/12 & -1/12 \end{Bmatrix}$$

3. Sharpening of a Defined Size Details on Image

This filter performs convolution transformation of the image through a user defined multiplication factor. As a result, all details of a user defined size are sharpened. The size of processed image detail may be defined through available editing submenu windows for X and Y dimensions.

$$I_{out} = I_{in} * \vartheta * \left( I_{in} - \sum_\Omega I_{in}/(m*n) \right), \quad (14)$$

where $\vartheta$ is the user defined multiplication factor and $\Omega$ is the $m\times n$ filter box 4. Sharpening of a Low Contrast Details This filter performs convolution transformation of the image and belongs to a spatial domain filters. The filtering is performed through a user defined multiplication Factor and automatically calculated special parameter. This parameter is a ratio of a current pixel value to Mean Square Deviation of a pixel value calculated for the given size of the pixel aperture (or filter box). As a result, all details of a user defined size are sharpened. The size of the processed image detail may be defined through available for editing submenu windows for X and Y dimensions.

$$I_{out} = I_{in} * \vartheta * \mu * \left( I_{in} - \sum_\Omega I_{in}/(m*n) \right), \quad (15)$$

where $\vartheta$ is factor and $\mu$ is $$\left( \sum_\Omega I_{in}/(m*n) \right) \Big/ \sigma_\Omega$$

5. Edge Enhancement Filter

This edge enhancement filter belongs to a non-linear range filter. User defines the size of the filter box. This filter provides two regimes, selected by the user, If the default regime Strong is changed by the user to regime Weak, the filter will change the processing method to avoid images noise impact in certain high frequencies.

$$I_{out} = Sup_\Omega, \text{when } I_{in} > 1/2*(Sup_\Omega + I_\Omega)$$

$$I_{out} = Inf_\Omega, \text{when } I_{in} \leq 1/2*(Sup_\Omega + Inf_\Omega) \quad (16)$$

where $Sup_\Omega$ is maximum brightnesss within filter box and $Inf_\Omega$ is minimum brightness within filter box 6. Edge Detection This edge detection filter belongs to modified Laplacian omnidirectional edge detection convolution filters. User defines the size of the filter box. This filter performs edge detection of the image through a user defined Factor. The Factor is used for convolution mask values calculations 7. Dilation Filters Both filters belong to morphological class and are inversive to each other. The first one should be used for image light elements dilation, the second one—for dark elements dilation. If the default regime Strong is changed by the user to regime Weak, both filters will change the processing method to avoid images noise impact in certain high frequencies. In general:

$$I_{out} = Sup_\Omega \text{ or } I_{out} = Inf_\Omega \quad (17)$$

8. Low Frequency

This filter represents a convolution transformation of modified Gaussian type. It belongs to a class of linear filters in frequency domain. The size of pixel box or aperture is defined by the user for X and Y dimensions. The filter is used often for certain frequencies noise reduction. In general:

$$I_{out} = \left( \sum_\Omega I_{in}/(m*n) \right) \quad (18)$$

9. Gradient/Modified Sobel Edge Detection Filter

This filter belongs to a non-linear edge-detection class. The filter uses a technique with partial derivatives replacement with their estimates. It is known in image processing as a Sobel filter. The size of the pixel box or aperture defined by the user for X and Y dimensions. This filter performs convolution transformation of the image through a user defined amplification Factor. The user also is provided with the ability to set a binarization Threshold if a correspondent check-box is marked. The threshold serves as a modification to the classic Sobel filter and enables the user to find right flexibility for the edge detection process. If the threshold is used the outcome of transformation will be a binary image. The default but modifiable masks are:

$$C_{mn} = \begin{Bmatrix} 1 & 0 & -1 \\ 2 & 0 & -1 \\ 1 & 0 & -1 \end{Bmatrix} \quad C_{mn} = \begin{Bmatrix} -1 & -2 & -1 \\ 0 & 0 & 0 \\ 1 & 2 & 1 \end{Bmatrix}$$

10. Shading Correction

This filter belongs to a smoothing class filter. The size of the pixel box or aperture is defined by the user for X and Y dimensions. The filter is modified from a classical type shading correction filter by enabling the user with shifting capability. If check-box Shift is marked the user will be able to change the default value of the shift to a custom one. This filter is very handy for elimination of a negative lighting impact which sometimes occurs during the image acquisition process.

$$I_{out} = \left(I_{in} - \sum_{\Omega} I_{in}/(m*n)\right) + \text{Shift,} \tag{19}$$

where Shift by default is 127

11. General or Universal Filter

This is a convolution type filter with a user controlled size of the kernel and the weights mask values. The default size of the kernel is 9×9. For the user's convenience, the convolution mask contains default typically used weights values. Pushbutton activates the customization regime when the user is able to modify dimensions of the mask and then modify default weights in the convolution mask.

12. Median (3×3) Filter

Moving median (or sometimes referred as rank) filter produces as an output the median, replacing a pixel (rather than the mean), of the pixel values in a square pixel box centered around that pixel. The filter is a non-linear type filter with the filtration window dimensions of 3×3. Usually used to eliminate very small details of the image sized at 1-2 pixels.

13. Median (5×5) Filter

Similar to the filter described above, but with the filtration window dimensions 5×5. Usually used to eliminate small details of the image sized at up to 5 pixels.

14. General Median Filter

This filter is similar to the filters described above, but with the filtration window dimensions set by the user. The size of eliminated details depend on the size of the set filtration window.

15. Psuedomedian Filter

This filter is similar to median type filters described above. However it provides rectangular filtration window controlled by the user and performs transformation in a two pass algorithm.

Figure 8:
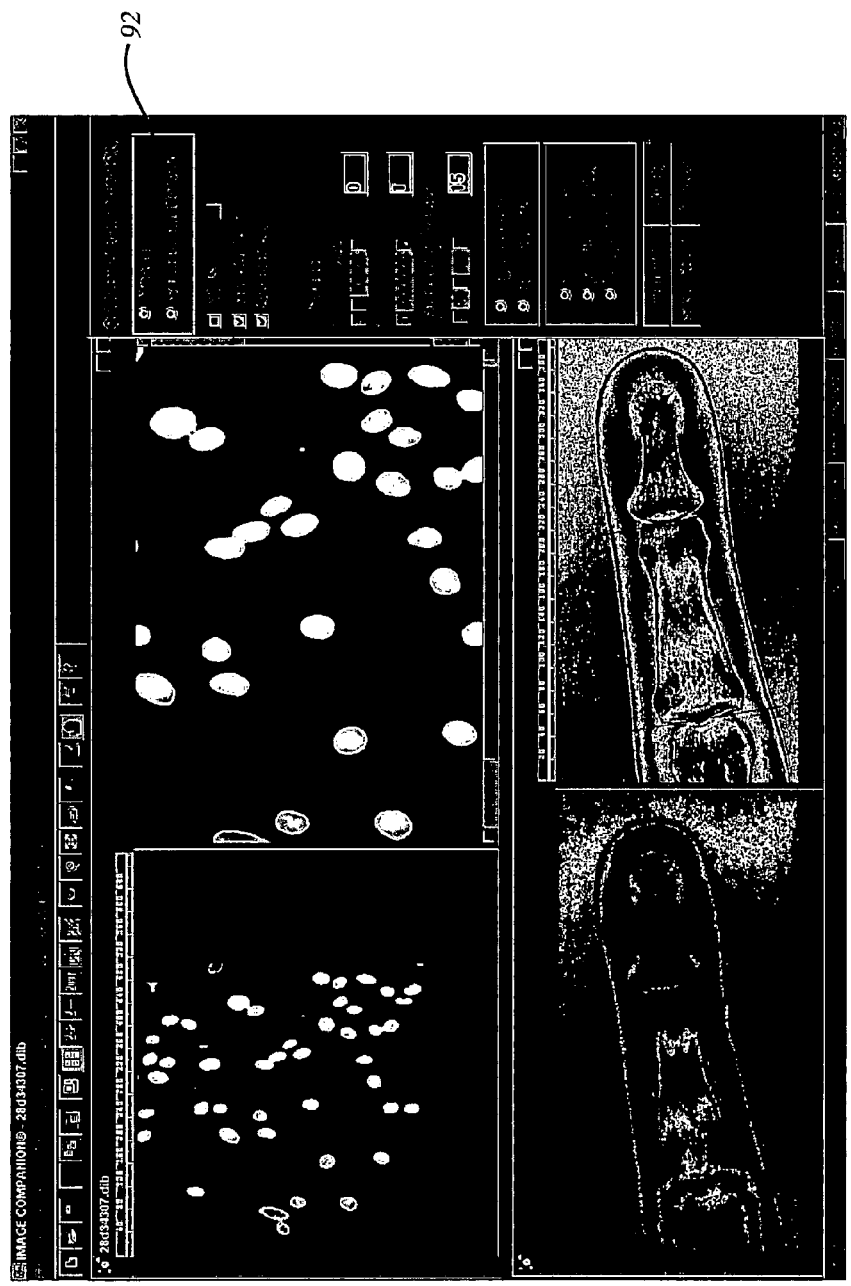
FIG. 8 is a screen display of user configured object definition according to one embodiment of the invention and which may be generated by the system of FIG. 2.

User control of object definition (corresponding to module 34 of FIG. 2) is illustrated in FIG. 8. By selecting one of the checkboxes 92, the user implements manual or semi-automatic object definition. In manual mode, slidebars allow the user to select a brightness range of pixels. All pixels outside this range are considered background. An object is thus defined as a connected set of pixels having brightness values in the user defined range. Background pixels may be reassigned a zero brightness value. In the automatic mode, the user interface for which is illustrated in FIG. 8, the thresholds are calculated automatically by the system from the image histogram. In this mode, the system may allow the user to set up multiple thresholds by setting their values manually or by choosing their sequential numbers from the automatically calculated table of thresholds.

As was the case with the filtering process, the image (or region of interest) is displayed as the object definition function is applied. Those of skill in the art will understand that a wide variety of techniques for assigning pixels to objects or background are known and used, any one of which now known or developed in the future may be used in conjunction with the present invention.

Figure 9:
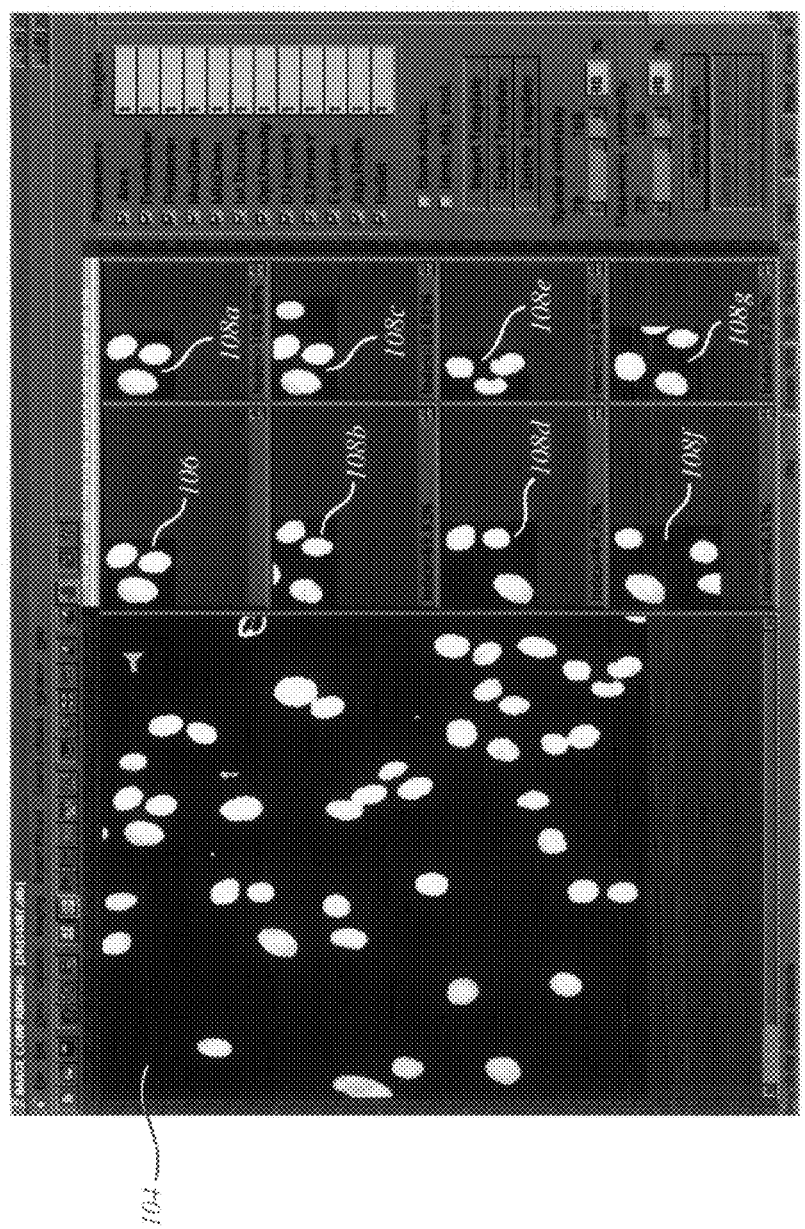
FIG. 9 is a screen display of user configured object searching and comparison according to one embodiment of the invention and which may be generated by the system of FIG. 2.

After objects are defined/detected, parameter sets are calculated for each object, and then comparisons are possible to find similar objects (or object clusters as discussed above) in either the same image or in different images. This is illustrated in FIG. 9, which shows a display of the original image 104 after filtering and object segmentation, as well as the template 106 selected for comparison to objects in the remainder of the image. In this example, the template 106 is a three object cluster. Also provided in this screen display are seven displays 108a-g which display in rank order the seven objects of the image most similar to the template object. Also displayed at 110 is a list of the parameters used in the comparison and the weights assigned to them for the comparison process. These weights may be manually set, or they may be set via a statistical process which is described in further detail below.

The actual comparison process which defines the degree of template similarity may, for example, be performed with the following formulas. For templates consisting of one individual parameterized object, a parameter difference vector may be computed which has as each element the difference between the parameter values divided by the maximum difference observed between the template object and all objects being compared to the template.

$$\Delta_{it}(P_{i t},P_j)/\Delta_{max}(P_{i t},P_k), \tag{20}$$

where
P is a parameter-vector; $_{it}$ is the index of template object; $_k$=1, . . . , L; L is all objects that the template object is being compared to; and $_j$ is the index of specific object being compared to template object.

A numerical similarity may then be computed using either a modified form of Euclidean or Minkowski line metrics or as modified Voronin formula as set forth below:

$$\begin{cases} \left(\sum_{k=1}^{L}(p_k^t - P_k^t)^s * \omega_k\right)^{1/s} \\ \text{and} \\ (P_i - P_k)^T W^{-1}(P_i - P_k), \\ \text{where } W \text{ is the covariation matrix;} \\ \omega \text{ is a statistical weight} \end{cases} \tag{21}$$

and in our modification is $$p = p_k^t / (\max p_k - \min p_k)$$

For multi-object templates or entire images, the spatial relationship between selected objects of the template to other objects in the template may be numerically characterized and effectively added as one or more additional subvectors of the object parameter vector. The overall similarity between a multi-object template and object clusters in the image database, may, in some embodiments of the invention be calculated as follows:

$$\zeta = \sum_{j=1}^{Z} \varpi * \text{abs}(\eta_{ij}^t)/Z, \quad (22)$$

where $Z$ – number of components, $\eta_{ij}^t = 1 - \text{abs}(\Delta_i^t - \Delta_j^t)/(\text{max}\Delta_t - \text{min}\Delta_t),$ $$\Delta^t = \begin{cases} 1, & \text{when abs}(\Delta_i^t - \Delta_j^t) \le \varepsilon_t \\ 0, & \text{else} \end{cases}$$

$\epsilon$ is a thresholds and/or tolerances vector, $\tilde{\omega}$ is a weights vector This formula combines not only parametric similarity but spatial similarity also. For spatial similarity the closeness of the position and pattern fit for objects of the template and objects of the database are numerically evaluated. The mathematical method for parameterizing these spatial relationships may, for example, use some simple Euclidean distances between objects for primitive cases and up to pattern fit calculations based on second, third, or fourth moments of inertia for comparable components in complex cases.

Once the objects are parameterized and the template is defined as either a single object or a cluster of objects, the comparison calculation involves the mathematical generation of a value which characterizes how "similar" two vectors or matrices of numbers without further reference to the meaning associated with those numbers. A wide variety of mathematical techniques are available to perform such a numerical characterization, and different approaches may be more suitable than others in different contexts. Thus, the specific formalism used to mathematically define and quantify similarity between number sets may vary widely in different embodiments of the invention and different techniques may be appropriate depending on the application.

As discussed above, the weight assigned to a given parameter during this comparison process may be manually set by the user or set using a statistical method. The statistical method is especially useful when the database of images includes a large number of objects which have been characterized as having or not having a characteristic trait, such as an area of skin pigmentation is either melanoma or not melanoma, or which have been characterized numerically as more similar or less similar to a "model" object. When this data is available, it can be analyzed to determine how strongly different parameters of the parameter set values correlate with the presence or absence of the specific trait.

The weight used for a given parameter in the comparison process may thus be derived from the values of the parameter vectors associated with the detected objects in the image database.

In using this method a system is represented as a totality of factors. The mathematical simulation tools are correlation, regression, and multifactor analyses, where the coefficients of pairwise and multiple correlation are computed and a linear or non-linear regression is obtained. The data for a specific model experiment are represented as a matrix whose columns stand for factors describing the system and the rows for the experiments (values of these factors).

The factor Y, for which the regression is obtained, is referred to as the system response. (Responses are integral indicators but theoretically, any factor can be a response. All the factors describing the system can be successively analyzed.). The coefficients of the regression equation and the covariances help to "redistribute" the multiple determination coefficient among the factors; in other words the "impact" of every factor to response variations is determined. The specific impact indicator of the factor is the fraction to which a response depending on a totality of factors in the model changes due to this factor. This specific impact indicator may then be used as the appropriate weight to assign to that factor (i.e. parameter of the parameter set associated with the objects).

The impact of a specific factor is described by a specific impact indicator which is computed by the following algorithm:

$$\gamma_j = \alpha *[b_j * c_{0j}], j=1,2,\ldots,k \quad (23)$$

where $\gamma$ is the specific impact indicator of the j-th factor; k is the number of factors studied simultaneously; $b_j$ is the j-th multiple regression coefficient which is computed by the formula $$X_0 = a + \Sigma b_j * X_j, \quad (24)$$

where $X_0$ is the system response to be investigated, a is a free term of the regression, and $X_j$ is the value of the j-th factor. The coefficient $\alpha$ of the equation is computed by the formula $$\alpha R^2, [\Sigma_j|b_j * c_{0j}|] \quad (25)$$

where R is the coefficient of multiple determination computed by the formula $$R = [(n^2 * \Sigma j b_j * c_{0j})/(n * \Sigma_j x^2_{0j} - (\Sigma_j x_{0i})^2)]^{1/2}, \quad (26)$$

where n is the number of observations, which cannot be below (2*K); $x_{0i}$ is the value of the system response in the i-th observation, $c_{0j}$ is the covariance coefficient of the system response indicator and the j-th factor. It is given by the relation $$c_{0j} = (n * \Sigma_i x_{0i} * x_{ji} - \Sigma_i x_{0i} * \Sigma_i x_{ji})/n^2 \quad (27)$$

The specific contribution indicator is obtained mainly from the coefficient of multiple determination, which is computed by the formula $$R^2 = (\Sigma_j b_j * c_{0j})/D^2 \quad (28)$$

where $D^2$ is the response variance. The specific impact of the j-th factor on the determination coefficient depends only on the ratio of addends in this formula. This implies that the addend whose magnitude is the largest is associated with the largest specific impact. Since the regression coefficients may have different signs, their magnitudes have to be taken in the totals. For this reason, the coefficients $\gamma$ of the specific impact are bound to be positive. However, it is important that the direction in which the factor acts by the computed $\gamma$ is dictated by the sign of the regression coefficient. If this sign is positive, the impact on the response variable is positive and if it is not, the increase of the factor results in a reduction of the response function. The influence of the background factors, which are not represented in the data, is computed by the formula $$\tilde{\gamma}_i = 1 - \Sigma_j \gamma_j. \quad (29)$$

The importance of the $\gamma$ is determined from the relation for the empirical value of the Fisher criterion $$F_j = (\gamma_j * (n-k-1))/(1-\Sigma_j \gamma_j). \quad (30)$$

A rearrangement of the initial data matrix at every experimental step makes it possible to investigate successively the dynamics of the significance of the impact the factors have on all system indicators that become responses successively. This method increases the statistical significance of the results obtained from the algorithm for the recomputation of the initial data matrix. The algorithm embodies serial repeatability of the experiments by fixing the factors at certain levels. If the experiment is passive, the rows of the initial matrix are chosen in a special way so that, in every computation, rows with the closest values of factors (indicators) influencing the response are grouped together. The dynamics of the specific contributions is computed by using the principle of data elimination.

In the proposed way, the computation of the dynamics of the insignificant information is gradually eliminated. The value of $\gamma$ does not change remarkably until the significant information is rejected. A dramatic reduction of $\gamma$ is associated with a threshold with which this elimination of useful information occurs. The algorithm of this operation is an iterative $\gamma$ recomputation by formula (23) and a rejection of information exceeding the threshold computed. In the algorithm, the significance of the result and of the information eliminated is increased by recomputing the initial data matrix into a series-averaged matrix, the series being, for instance, the totality of matrix rows grouped around the closest values of the factor in the case of a passive factorial experiment. The series may also consist of repeated changes of the indicator with the others fixed at a specified level. Because in further discussion the series-averaged matrix is processed in order to obtain final results, the compilation of series from the data in a field is a major task for the user because, both, the numerical and meaningful (qualitative) result of the computation may be influenced. With increasing threshold the amount of rejected information also increases, therefore one has to check whether the amount of information in the series-averaged matrix is sufficient, see below. Consequently, the information on the factor considered in this version of the method is rejected by the formula $$X_{1i} = [\Sigma_p X_{1ip} - m^* h]/n_i, \, p=1,2,\ldots, m; \, i=1,2,\ldots,N,$$

where $X_{1i}$ is the value of the i-th series in which the factor $X_1$ is observed and for which the critical (rejection) threshold is determined after the elimination of data with a threshold of H; $n_i$ is the number of observations in the i-th series; m is the number of values of the $X_1$ which exceed h and ($0 \le m \le n_i$); N is the number of observation series (rows of the N*(K+1) matrix of the initial information, where K is the number of factors investigated simultaneously.)

The invention thus provides image searching and comparison based in a much more direct way on image content and meaning than has been previously available. In addition, using the described method of weights calculations for targeting similarities between a multi-component template and a database of images in medical fields is much more mathematically justified and sound than neural network techniques used for the same purposes. That is important to understand because template matching may be used in such applications to decrease the difficulty of database creation and search, and improve early cancer diagnostics, early melanoma detection, etc.

As set forth above, diagnosis or estimation of level of likelihood of potential disease states is facilitated by noting that an object in a query image is or is not similar to objects previously classified as actual examples of the disease state. In some embodiments, diagnosis or level of likelihood of potential disease states is facilitated by computing a numerical score which is indicative of the likelihood that a particular diagnosis (e.g. malignant melanoma or benign growth, benign breast lesion or carcinoma) is correct. This score may be computed by an analysis of the numerical similarity scores between an object or objects in the query image and previously classified objects in the database. Several new methods are proposed as set forth below.

Algorithm 1: This is a first order ranking method, essentially a binary classification of the query object. The software calculates and retrieves the $T_\psi$ closest matches in the database to the unknown object. The database objects were previously detected, defined and quantified. Then the rank is assigned according to a rule: if more than a half of the closest template objects $T_\psi$ have been diagnosed as no disease then the score for the unknown object shall reflect no disease finding, otherwise the score reflects disease or its likelihood.

Algorithm 2. This is a simple Averaging Ranking Scoring system. Continuum similarity values for the closest $T_\psi$ templates objects with known findings are substituted by their dichotomic ranks (e.g.—1 for benign or 5 for malignant, or 1 for presence of the disease and 0—for its absence). Then the assigned score is an average of the $T_\psi$ ranks.

Algorithm 3. Scoring with the penalty function. The method uses only the maximum number $\Gamma\Omega$ of closest templates objects that corresponds to the highest ranking value $\tau_{max}$ in the scoring range. The values of calculated similarities between each template with known finding and the unknown object is substituted with the values that are calculated as follows:

For Templates of highest $\tau_{max}$:

$\tau_{max}$-Penalty*Relative Similarity;

For Templates of $\tau_{min}$:

$\tau_{min}$+Penalty*Relative Similarity.

For example, if $\tau_{max}$ is equal 5 and $\tau_{min}$ is equal 1 and the Relative Similarity based retrieved closest matches for cluster of 6 are (62.24% 60.78% 60.48% 59.68% 59.49% 59.23%) with diagnostic findings as follows (benign malignant benign benign benign benign malignant) then the score for. i.e. second template in the cluster will be equal to 5+(5−1)*(60.78−100)/100=3.431.

Algorithm 4. Averaging with weights for position with fixed retrieved templates cluster method. The software calculates and retrieves the $\Gamma_\psi$ closest matches to the unknown object that represents the manifestation of the disease (i.e. lesion, skin growth, etc). These objects were detected, defined and quantified. Continuum similarity values for the closest $\Gamma_\psi$ templates objects with known findings are substituted by their dichotomic ranks (i.e. −1 for benign or 5 for malignant, or 1 for presence of the disease and 0—for its absence). Then the assigned score is an average of the $\Gamma_\psi$ ranks, however each rank is multiplied by the evenly distributed weight calculated for its position in retrieved cluster. Each weight can be calculated in different ways—for example as follows: for each position above the middle position of the cluster the current rank gets its weight increased by 1, for every position below the middle position of the cluster the current rank gets its weight decreased by 1 (i.e. if the cluster $N_c$ is 7 then the score of the closest $\Gamma_\psi$ template object will have its weight of (7+1+1+1)/7=10/7. In other words if we have the following sequence of the closest matches malignant-benign-benign-malignant-malignant-benign-malignant in $N_c$=7 templates cluster and malignant is indicated by the score 5 and benign is indicated by the score 2 then the calculated total score will be (5*10/7+2*9/7+2*8/7+5*7/7+5*6/7+2*5/7+5*4/7) 17=3.653).

Algorithm 5. Averaging with weights for position method with floating retrieved templates cluster method. The method is similar to Algorithm 4 except number $N_c$ of templates in each retrieved cluster is truncated. The truncation could be done by setting Relative Similarity threshold to, say, 80% or 90%. This way all templates with Relative Similarity below the threshold will not be considered and the value of $N_c$ will not be constant like in Algorithm 4.

Figure 10:
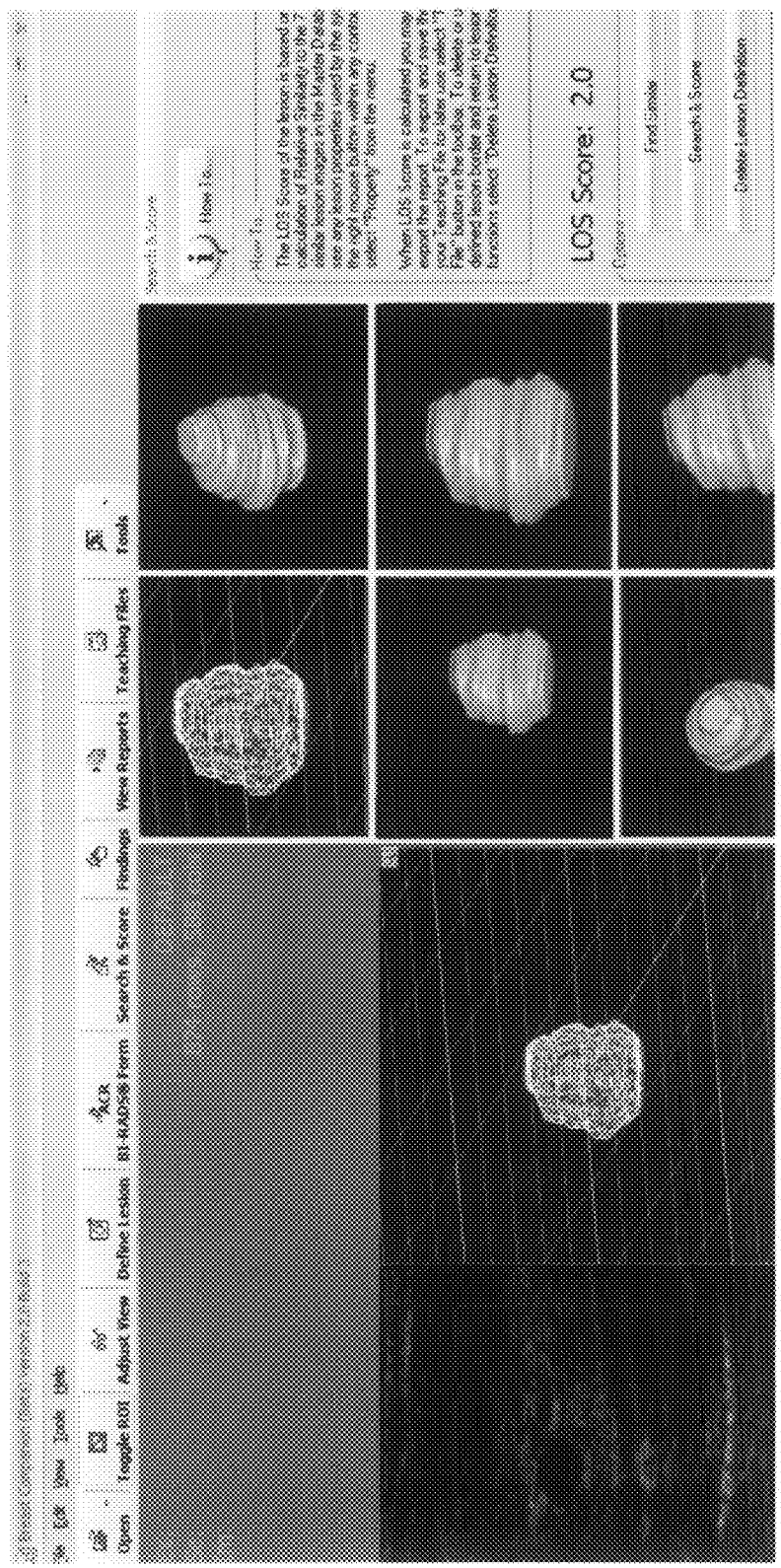
FIG. 10 is a screen display of user configured object searching, comparison and scoring similarity according to one embodiment of the invention and which may be generated by the system of FIG. 2.

In the example of FIG. 10, existing multiple slices of 3D ultrasound image of a breast lesion were processed by the system, segmented and the selected few scored against digital database of templates with known findings. The result of the database search, retrieval and scoring was displayed in a form of 7 closest matches found and overall score is produced (in our case 2—benign) by one of the five scoring methods described herein below. Then the system rendered 3D image of the processed lesion slices facilitating further quantification of the lesion such as analyses of volume, vortex as well as estimations of the texture and curvature of the lesion surface. It is possible to compare and quantify relative similarity not only individual slices of the lesion but also the rendered 3D lesion or mass as a whole object.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof

What is claimed is:

1. A method for facilitating diagnosis or suspicion of a condition related to an X-ray, MRI, mammography, or ultrasound, comprising:
   processing user input to identify or define an object of interest in a first display image, the object of interest being located within the first display image and representing a candidate condition or indication for diagnosis or suspicion of the condition;
   displaying the object of interest in a first display;
   determining at least one imaging parameter based on at least one measurement of the object of interest;
   displaying, near the first display, a plurality of additional images from an identified database, wherein each of the plurality of additional images comprises one or more objects and each of the plurality of additional images is identified based on mathematically generating a value which characterizes a similarity measurement between the at least one imaging parameter of the objects of interest and the at least one stored parameter of an object within the corresponding additional images;
   spatially arranging the plurality of additional images according to the similarity measurement and
   selecting, by a user, at least one of a plurality of image sharpening options with checkboxes;
   outputting a first result for a first analysis of the user input based on pixel location;
   outputting a second result for a second analysis of the user input based on the first result of the first analysis; and
   outputting a numeric score that indicates the likelihood that a disease is associated with the user input, wherein the similarity measurement is based on the first result and the second result, and the similarity measurement is calculated with a modified Voronin formula.

2. The method of claim 1, wherein each of the plurality of additional images is smaller than the first display image and wherein the first display image is displayed simultaneously to the plurality of additional images.

3. The method of claim 2, wherein each of the plurality of additional images is a portion of a full representation of an original referenced images.

4. The method of claim 1, wherein the mathematical generation of a value which characterizes the similarity measurement fails to refer to the meaning associated with the at least one imaging parameter.

5. The method of claim 4, wherein the at least one imaging parameter comprises a parameter that is a numeric representation of at least one of geometry, texture and density of the first display image.

6. The method of claim 1, wherein:
   the object of interest comprises multiple components, and
   a multi-object template is used to determine the similarity measure based on at least a spatial relationship between one or more objects of the multi-object template to other objects in the multi-object template.

7. The method of claim 1, wherein the identified database is a reference library of cases with known or confirmed diagnosis or condition.

8. The method of claim 1, further comprising selecting the imaging parameters based on a pixel analysis.

9. The method of claim 8, wherein the pixel analysis is a pixel location analysis.

10. The method of claim 8, wherein the pixel analysis is an image geometry, image texture, or image density analysis.

11. The method of claim 1, further comprising determining at least one secondary parameter as a function of the at least one imaging parameter, wherein each the plurality of additional images is identified based on both the at least one imaging parameter and the at least one secondary parameter.

12. The method of claim 11, wherein the at least one secondary parameter is a risk factor, an age of a patient, or a disease history of a patient.

13. The method of claim 1, wherein the similarity measurement between the at least one imaging parameter of the objects of interest and the at least one stored parameter of an object is measured by Mikowski line metrics or measured by Hamming distance.

14. A method for facilitating diagnosis or suspicion of a condition related to an X-ray, MRI, mammography, or ultrasound, comprising:
   displaying a first image comprising an object to a user; and
   displaying, near the first image, a plurality of additional images from an image repository, wherein:
   each of the plurality of additional images comprises one or more objects,
   each of the plurality of additional images is identified based on a mathematically generating of a value which characterizes a similarity measurement between the at least one stored parameter of an object within the corresponding additional image and the at least one imaging parameter of an object of interest of the first image,
   each of the plurality of additional images corresponds to a known diagnosis, the plurality of additional images are spatially arranged according to the similarity measurement and
   selecting, by a user, at least one of a plurality of image sharpening options with checkboxes;
   outputting a first result for a first analysis of the user input based on pixel location;
   outputting a second result for a second analysis of the user input based on the first result of the first analysis; and
   outputting a numeric score that indicates the likelihood that a disease is associated with the user input, wherein the similarity measurement is based on the first result and the second result, and the similarity measurement is calculated with a modified Voronin formula.

15. The method of claim 14, wherein the at least one imaging parameter comprising a parameter selected from a group consisting of a numeric representation of geometry, texture and density.

16. The method of claim 14, wherein each of the plurality of additional images is smaller than the first image and wherein the first image is displayed simultaneously to the plurality of additional images.

17. The method of claim 14, wherein each of the plurality of additional images is a portion of a full representation of an original referenced image with known or confirmed diagnosis or condition.

* * * * *